United States Patent [19]
Arnaud et al.

[11] Patent Number: 6,103,221
[45] Date of Patent: Aug. 15, 2000

[54] PHOTOPROTECTIVE/COSMETIC COMPOSITIONS COMPRISING BENZOTRIAZOLE-SUBSTITUTED SILICON COMPOUNDS AND BENZOIC TRIACID TRIESTERS

[75] Inventors: Pascal Arnaud, L'Hay les Roses; Martine Viard, Paris, both of France

[73] Assignee: Societe L'Oreal S.A., Paris, France

[21] Appl. No.: 09/397,514

[22] Filed: Sep. 17, 1999

[30] Foreign Application Priority Data

Sep. 24, 1998 [FR] France .................. 98 11946

[51] Int. Cl.$^7$ .............................. A61K 7/42; A61K 7/44; A61K 7/00
[52] U.S. Cl. .............................. 424/59; 424/60; 424/400; 424/401
[58] Field of Search ............................. 424/59, 60, 400, 424/401

[56] References Cited

U.S. PATENT DOCUMENTS 4,940,574 7/1990 Kaplan ............................ 424/59

FOREIGN PATENT DOCUMENTS 0 711 779  10/1995  European Pat. Off. .
WO94/06404  3/1994  WIPO .

*Primary Examiner*—Shelley A. Dodson
*Attorney, Agent, or Firm*—Burns, Doane, Swecker & Mathis, L.L.P.

[57] ABSTRACT

Topically applicable cosmetic/dermatological sunscreen compositions well suited for the UV-photoprotection of human skin and/or hair against the damaging effects of UV-A and UV-B irradiation, particularly solar radiation, comprise (i) a UV-photoprotecting effective amount of at least one solubilized organolipophilic silicon compound, whether silane or organopolysiloxane, bearing a benzotriazole function substituent and (ii) an amount of at least one benzoic triacid triester effective to (substantially) dissolve said at least one organolipophilic silicon compound.

32 Claims, No Drawings

PHOTOPROTECTIVE/COSMETIC COMPOSITIONS COMPRISING BENZOTRIAZOLE-SUBSTITUTED SILICON COMPOUNDS AND BENZOIC TRIACID TRIESTERS

CROSS-REFERENCE TO PRIORITY APPLICATION

This application claims priority under 35 U.S.C. §119 of FR-98/11946, filed Sep. 24, 1998, hereby expressly incorporated by reference.

CROSS-REFERENCE TO COMPANION APPLICATION

Copending application Ser. No. 09/397,513 [Attorney Docket No. 016800-310], filed Sep. 17, 1999 concurrently herewith and assigned to the assignee hereof.

BACKGROUND OF THE INVENTION

Technical Field of the Invention

The present invention relates to novel cosmetic compositions for topical application, in particular for the photoprotection of the skin and/or the lips and/or superficial body growths/hair against ultraviolet radiation (such compositions hereinafter simply being designated antisun or sunscreen compositions), and to the use of same for the cosmetic applications indicated above.

More especially, this invention relates to novel cosmetic compositions exhibiting improved photoprotective capacity, comprising, formulated into a cosmetically acceptable support therefor: (i) at least one silicon compound bearing a benzotriazole function substituent and constituting a lipophilic organic sunscreen, and (ii) a specific judiciously selected oil, present in a predetermined amount, and which comprises a benzoic triacid triester.

Description of the Prior Art

It is known to this art that light radiation of wavelengths of from 280 nm to 400 nm permits tanning of the human epidermis and that light radiation of wavelengths of from 280 to 320 nm, i.e., UV-B irradiation, causes skin burns and erythema which may be harmful to the development of a natural tan; this UV-B radiation should thus be screened from the skin.

It is also known to this art that UV-A radiation, of wavelengths of from 320 to 400 nm, promotes tanning of the skin, but is also liable to induce an adverse change therein, especially in the case of sensitive skin or skin which is continually exposed to solar radiation. UV-A rays in particular cause a loss of elasticity of the skin and the appearance of wrinkles, promoting a premature aging of the skin. Such irradiation promotes triggering of the erythemal reaction or amplifies this reaction in certain individuals and may even be the cause of phototoxic or photoallergic reactions. It is thus desirable to also screen out UV-A radiation.

Many and varied cosmetic compositions for the photoprotection (UV-A and/or UV-B) of the skin are known to this art.

These known sunscreen compositions contain, in various concentrations and depending on the nature of the pharmaceutical form selected, one or more standard lipophilic and/or hydrophilic organic screening agents capable of selectively absorbing harmful UV radiation, these screening agents (and the amounts thereof) being selected as a function of the desired protection factor (the protection factor (PF) being expressed mathematically as the ratio of the irradiation time required to reach the erythema-forming threshold with the UV screening agent to the time required to reach the erythema-forming threshold without UV screening agent).

Lipophilic UV organic screening agents which are particularly advantageous in antisun cosmetics and which are highly active both in the UV-A range and in the UV-B range are described in EP-A-0,392,883; EP-A-0,660,701; EP-A-0,708,108; EP-A-0,711,778; EP-A-711,779.

These are silanes or polyorganosiloxanes substituted by a benzotriazole function. They present the particular feature but also the drawback of being solid at room temperature. Consequently, including same in an antisun cosmetic composition entails certain constraints as regards their formulation and implementation, in particular as regards determining solvents for properly dissolving them. In this respect, oils are typically selected such as esters, and more particularly $C_{12}$–$C_{15}$ alkyl benzoates ("Finsolv TN" marketed by Finetex), or triglycerides and in particular $C_8$–$C_{12}$ fatty acid triglycerides ("Miglyol 812" marketed by Hüls), or monoalcohols or polyols such as ethanol, as well as mixtures thereof. Although providing solubilizing properties with respect to the aforesaid screening agents, these solvents nevertheless present the drawback of themselves having no intrinsic activity as regards screening out UV radiation, whether UV-A or UV-B irradiation.

Utilizing oils of the benzoic triacid triester type such as tridecyl trimellitate is known for the formulation of many cosmetic products comprising a fatty phase. Compare, in particular, EP-A-0,792,637 relating to lipsticks and EP-A-0,194,055 relating to the preparation of anhydrous cosmetic formulations free of mineral oil.

U.S. Pat. No. 4,940,577 describes this type of oil as constituting the fatty phase of transparent microemulsions of the water-in-oil type having a low water content and necessarily containing a specific phosphate ester as the sole emulsifier. These microemulsions are useful as antisun products based on organic UV screening agents such as octyldimethyl para-aminobenzoate, octyl cinnamate, octyl salicylate or 3-benzophenone, as well as self-tanning products.

And U.S. Pat. No. 4,940,574 describes this type of oil as an emollient in anhydrous antisun products having a high degree of protection, containing, in a silicone oil, a combination of two UV-B organic screening agents selected from among a cinnamate, a salicylate and a para-aminobenzoate and a UV-A organic screening agent of the benzophenone type.

SUMMARY OF THE INVENTION

It has now surprisingly and unexpectedly been determined that the photoprotective power of a lipophilic UV screening agent of the silicon derivative type substituted by a benzotriazole function is markedly enhanced by formulating such specific screening agents with a specific, judiciously selected oil which is a benzoic triacid triester, this oil being present in the compositions in an amount which is sufficient by itself to dissolve all of the screening agent(s).

Thus, the present invention features novel cosmetic or dermatological compositions which comprise, formulated into a cosmetically acceptable support therefor, (i) at least one lipophilic UV screening agent of the silicon derivative type bearing a benzotriazole functional group substituent, and (ii) at least one benzoic triacid triester in an amount which is sufficient by itself to dissolve all of said screening agent(s).

The present invention also features converting such compositions into products suited for protecting the skin and/or the lips and/or superficial body growths such as the hair, the eyelashes, the eyebrows or the nails against ultraviolet radiation, in particular solar radiation.

Too, this invention features formulating at least one benzoic triacid triester into improvedly photoprotective cosmetic compositions for protecting the skin and/or the lips and/or superficial body growths such as the hair, the eyelashes, the eyebrows or the nails against ultraviolet radiation, such compositions also comprising particular UV sunscreens, i.e., at least one silicon compound bearing a benzotriazole substituent.

DETAILED DESCRIPTION OF BEST MODE AND SPECIFIC/PREFERRED EMBODIMENTS OF THE INVENTION

More particularly according to the present invention, the silicon compounds substituted by a benzotriazole function are preferably silanes or siloxanes containing a benzotriazole function comprising at least one structural unit of formula (1) below:

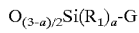  (1)

in which $R_1$ is an optionally halogenated $C_1$–$C_{10}$ alkyl radical, or a phenyl or trimethylsilyloxy radical; a is an integer ranging from 0 to 3, inclusive; and the symbol G is a monovalent radical directly bonded to a silicon atom and having the formula (2) below:

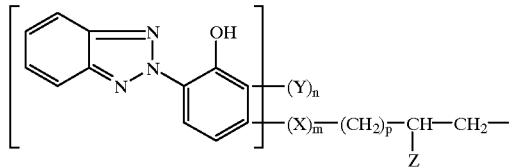  (2)

in which the radicals Y, which may be identical or different, are each a $C_1$–$C_8$ alkyl radical, a halogen atom, or a $C_1$–$C_4$ alkoxy radical, with the proviso that, in the latter instance, two adjacent groups Y on the same aromatic ring member can together form an alkylidenedioxy group wherein the alkylidene group contains 1 or 2 carbon atoms; X is O or NH; Z is hydrogen or a $C_1$-$C_4$ alkyl radical; n is an integer ranging from 0 to 3, inclusive; m is 0 or 1; and p is an integer ranging from 1 to 10, inclusive.

These compounds are described, in particular, in EP-A-0,392,883; EP-A-0,660,701; EP-A-0,708,108; EP-A-0,711,778; EP-A-711,779.

Preferably, the silicon derivatives according to the present invention belong to the general family of benzotriazole silicones which is described in EP-A-0,660,701.

One family or class of benzotriazole silicones which is particularly suitable according to the present invention is that which combines the compounds corresponding to formula (3) or (4) below:

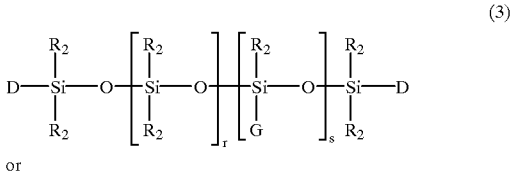  (3)

or

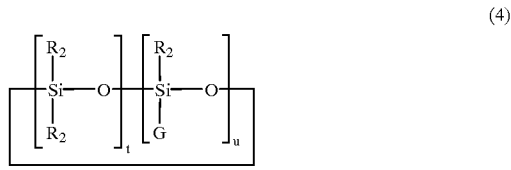  (4)

in which the radicals $R_2$, which may be identical or different, are each a $C_1$–$C_{10}$ alkyl, phenyl, 3,3,3-trifluoropropyl or trimethylsilyloxy radical, at least 80% by number of the radicals $R_2$ being methyl radicals; the radicals D, which may be identical or different, are each a radical $R_2$ or the radical G; r is an integer ranging from 0 to 50, inclusive, and a is an integer ranging from 0 to 20 inclusive, and if s=0, at least one of the two radicals D is a radical G; u is an integer ranging from 1 to 6, inclusive, and t is an integer ranging from 0 to 10, inclusive, with the proviso that t+u is greater than or equal to 3; and the radical G has the formula (2) above.

As will be seen from formula (2) above, bonding of the radical —(X)$_m$—(CH$_2$)$_p$—CH(Z)—CH$_2$— to the benzotriazole nucleus, which thus ensures attachment of said benzotriazole nucleus to a silicon atom of the silicone chain, may be at all of the available positions of the two aromatic rings of the benzotriazole:

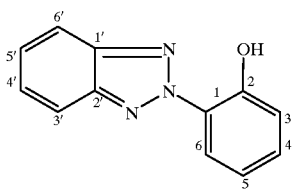

Preferably, this bonding is at position 3, 4, 5 (aromatic ring bearing the hydroxyl function) or 4' (benzene ring adjacent to the triazole ring), and even more preferably is at position 3, 4 or 5. In a preferred embodiment of the invention, the bonding is at position 3.

Similarly, attachment of the substituent unit or units Y may be at all the other available positions in the benzotriazole. However, preferably, this bonding is at position 3, 4, 4', 5 and/or 6. In a preferred embodiment of the invention, attachment of the unit Y is at position 5.

In formulae (3) and (4) above, the alkyl radicals may be linear or branched and selected in particular from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred alkyl radicals $R_2$ according to the invention are methyl, ethyl, propyl, n-butyl, n-octyl and 2-ethylhexyl radicals. Even more preferably, the radicals $R_2$ are all methyl radicals.

Among the compounds of formula (3) or (4) above, preferred are those corresponding to formula (3), namely, diorganosiloxanes containing a short linear chain.

Among the compounds of formula (3) above, preferred are those for which the radicals D are both radicals $R_2$.

Among the linear diorganosiloxanes within the scope of the present invention, particularly preferred are the random derivatives or well-defined block derivatives having at least one, and even more preferably all, of the following characteristics:

D is a radical $R_2$;

$R_2$ is alkyl and even more preferably is methyl;

r ranges from 0 to 15, inclusive; s ranges from 1 to 10, inclusive;

n is not zero and preferably is equal to 1, and Y is then selected from among methyl, tert-butyl and $C_1$–$C_4$ alkoxy;

Z is hydrogen or methyl;

m=0 or [m=1 and X=0];

p is equal to 1.

One family or class of benzotriazole silicones which is particularly preferred is that having the general formula (5) below:

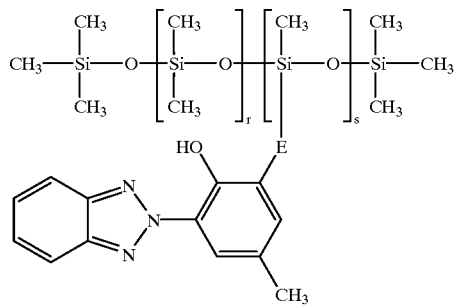
(5)

in which $0 \leq r \leq 10$; $1 \leq s \leq 10$; and E is the divalent radical:

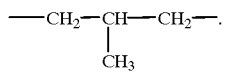

In a particularly preferred embodiment of the invention, the benzotriazole silicone is the compound (hereinafter referred to as compound (a)) having the following formula:

compound (a)

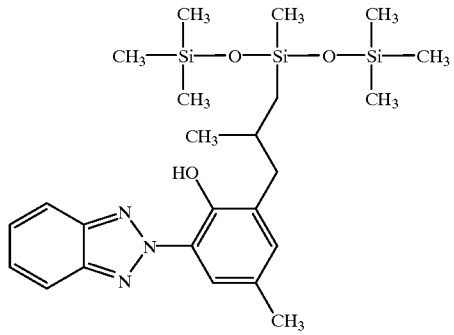

Processes which are suitable for the preparation of the compounds of formulae (1), (3), (4) and (5) are described, in particular, in U.S. Pat. Nos. 3,220,972, 3,697,473, 4,340,709, 4,316,033 and 4,328,346 and in EP-A-0,392,883 and EP-A-0,742,003.

The screening silicon compounds bearing a benzotriazole substituent are advantageously present in the compositions according to the invention in amounts ranging from 0.1% to 20%, preferably ranging from 0.2% to 15%, by weight, again relative to the total weight of the composition. According to an essential characteristic of the present invention, these compounds, whether alone or in admixture, should be present in the final composition in a fully, or substantially fully, dissolved form.

The benzoic triacid triesters according to the present invention are generally selected from among triesters of the benzoic triacid with linear or branched, saturated or unsaturated alcohols having from 3 to 30 carbon atoms, preferably from 8 to 18 carbon atoms. These have the general formula (I) below:

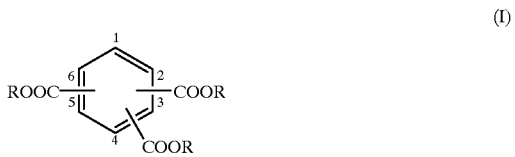
(I)

in which R is a linear or branched, saturated or unsaturated alkyl radical having from 3 to 30 carbon atoms and preferably from 8 to 18 carbon atoms.

They are more preferably selected from among the trimellitic acid esters having the general formula (II) below:

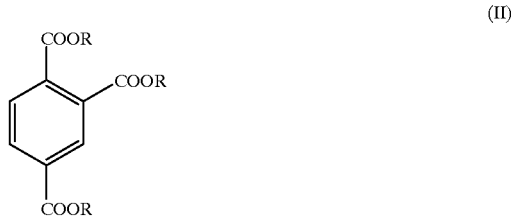
(II)

in which R is as defined in formula (I), and more particularly from:

2-Ethylhexyl trimellitate, such as the commercial product marketed under the trademark Bisoflex TOT by International Speciality Chemical;

Decyl trimellitate;

Triisodecyl trimellitate, such as the commercial product marketed under the trademark Dub TMI by Stéarineries Dubois;

2-Butylhexyl trimellitate, such as the commercial product marketed under the trademark Isofol Ester 1293 by Condea;

Tridecyl trimellitate, such as the commercial product marketed under the trademark Liponate TDTM by Lipo Chemicals; or Mixtures thereof.

This specific oil formulated in accordance with the present invention is advantageously present in the final compositions in amounts ranging from 0.1% to 99% by weight relative to the total weight of the composition, and preferably in amounts ranging from 0.5% to 50% by weight.

According to an essential characteristic of the compositions according to the invention, the benzoic triacid triester must be present in an amount such that it is sufficient by itself to dissolve all, or substantially all, of the silane or silicone screening agent containing a benzotriazole function, present in the composition. This minimum amount of solvent oil intended to ensure complete and stable dissolution of the solid screening agent can be conventionally determined from tests of solubility of said screening agent in this solvent.

In general, it should be appreciated that the concentrations of screening agent and of oil are selected such that the sun protection factor of the final composition is preferably at least 2.

The applications of the combination of benzoic acid triester/UV screening agent of the silicon derivative type containing a benzotriazole function, according to the invention, are manifold and concern all of the cosmetic and dermatological products.

The cosmetic/dermatological products of the invention are advantageously formulated into appropriate vehicle, diluent or carrier as solid, pasty or liquid compositions, in anhydrous or emulsion form.

Thus, the compositions of the invention can be in any pharmaceutical form normally employed for topical application, and in particular in the form of an oil; a suspension; a two-phase product, an oil-in-water or water-in-oil dispersion; a simple or complex emulsion (oil-in-water, water-in-oil, water-in-oil-in-water or oil-in-water-in-oil emulsion) such as a cream, a milk, a cream-gel, a salve, a lotion or an ointment; a vesicle dispersion; a powder; a cast or molded solid such as a stick or a compacted product; a foam or a spray.

The compositions according to the invention are advantageously used to make up and/or treat the skin both of the human face and body, the lips and superficial body growths such as the hair, the eyelashes, the eyebrows and the nails depending on the nature of the active agents used.

In particular, the compositions of the invention can be a tube of lipstick, a lip gloss which can be used as is or applied to a film of lipstick in particular to increase its gloss (which is known as a top coat). They can also constitute a fluid or solid foundation, a concealer product or product for the contours of the eyes, an eyeliner, a mascara, a face powder, an eyeshadow, a nail varnish, a free powder, a makeup product for the body or a care or cleansing product for the skin such as scrubbing products. The compositions can also contain cosmetic or dermatological active agents, in particular in order to impart to the composition a care or therapeutic aspect.

In another preferred embodiment of the invention, the subject compositions are formulated as lip products.

The compositions of the invention can also comprise conventional cosmetic additives and adjuvants selected, in particular, from among fatty substances, organic solvents, ionic or nonionic thickeners, softeners, antioxidants and in particular free-radical-scavenging antioxidants, opacifiers, stabilizers, emollients, silicones, fluoro compounds, α-hydroxy acids, antifoaming agents, hydrating agents, vitamins, fragrances, preservatives, surfactants, pigments, pearlescent agents, fillers, sequestering agents, polymers, propellants, basifying or acidifying agents, dyes, colorants, or any other ingredient usually included in cosmetics.

By the term "pigments" are intended white or colored, inorganic or organic particles which are insoluble in the liquid fatty phase and which impart color to and/or opacify the composition. By the term "fillers" are intended colorless or white, inorganic or synthetic, lamellar or non-lamellar particles. And by the term "pearlescent agents" are intended iridescent particles produced, in particular, by certain molluscs in their shell or else synthesized. These fillers and pearlescent agents serve in particular to modify the texture of the composition.

Exemplary inorganic pigments according to this invention, include titanium dioxide, zirconium oxide or cerium oxide, as well as zinc oxide, iron oxide or chromium oxide and ferric blue. Exemplary organic pigments include carbon black and barium, strontium, calcium (DC Red No. 7) and aluminum lakes.

Exemplary pearlescent agents include mica coated with titanium dioxide, with iron oxide, with natural pigment or with bismuth oxychloride, such as colored titanium mica.

Particularly exemplary are talc, mica, kaolin, Nylon (in particular Orgasol) powder, polyethylene powder, Teflon, starch, boron nitride, copolymer microspheres such as Expancel (Nobel Industrie), Polytrap (Dow Corning) and silicone resin microbeads (Tospearl from Toshiba, for example).

The fatty substances which are suitable for the compositions of the invention are generally selected, depending on the application envisaged, from among oils, waxes and gums or mixtures thereof.

The oils can by hydrocarbon-based and/or silicone and/or fluoro oils. These oils can be of animal, plant, mineral or synthetic origin. Exemplary such oils include hydrocarbon-based oils of animal origin, such as perhydrosqualene; plant or synthetic hydrocarbon-based oils, such as fatty acid triglycerides of 4 to 22 carbon atoms, for example heptanoic or octanoic acid triglycerides, hydrogenated coconut triglycerides and caprylic/capric acid triglycerides such as those marketed by Stéarineries Dubois or those marketed under the trademarks Miglyol 810, 812 and 818 by Dynamit; linear or branched hydrocarbons of mineral or synthetic origin, such as liquid paraffins and derivatives thereof, petroleum jelly, polydecenes, hydrogenated polyisobutene such as parleam; synthetic esters and ethers, in particular of fatty acids, such as the oils of formula $R_3COOR_4$ in which $R_3$ is a higher fatty acid residue having from 7 to 29 carbon atoms and $R_4$ is a hydrocarbon-based chain having from 3 to 30 carbon atoms, such as, for example purcellin oil, isopropyl myristate, 2-ethylhexyl palmitate, 2-octyldodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate, heptanoates, octanoates and decanoates of fatty alcohols; polyol esters such as propylene glycol dioctanoate, neopentyl glycol diheptanoate or diethylene glycol diisononanoate; and pentaerythritol esters; fatty alcohols having from 12 to 26 carbon atoms, for example octyldodecanol, 2-butyloctanol, 2-hexyldecanol, 2-undecylpentadecanol or oleyl alcohol; silicone oils, for example volatile or non-volatile, linear or cyclic polymethylsiloxanes (PDMSs) which are liquid or pasty at room temperature; mixtures thereof.

The waxes are advantageously hydrocarbon-based waxes, silicone waxes and/or fluoro waxes and can be of plant, mineral, animal and/or synthetic origin. In particular, they have a melting point of greater than 25° C. and preferably greater than 45° C.

Exemplary waxes according to the invention, include oxypropylenated or non-oxypropylenated, acetylated or non-acetylated lanolin, beeswax, carnauba wax, candelilla wax, paraffin, lignite or microcrystalline waxes, ceresin or ozocerite; synthetic waxes, for example polyethylene waxes and Fischer-Tropsch waxes or octacosanyl stearate, silicone waxes such as alkyl- or alkoxydimethicone having from 16 to 45 carbon atoms.

The nature and amount of the gums or waxes depend on the desired mechanical properties and textures of the subject compositions. For example, the composition can contain from 0% to 50% by weight of waxes relative to the total weight of the composition, and preferably from 5% to 30%.

The cosmetic compositions according to the invention are useful antisun or sunscreen products for photoprotecting the skin and/or the hair against the harmful effects of UV radiation. These products can be formulated as a suspension or dispersion in solvents or fatty substances, as a nonionic vesicle dispersion or, alternatively, as an emulsion, preferably of oil-in-water type, such as a cream or a milk, or as a salve, a salve, a gel, a lotion, a cream-gel, a solid tube such as a stick, an aerosol foam or a spray.

The compositions in accordance with the invention can also contain one or more additional hydrophilic or lipophilic sunscreens which are active in the UWA and/or UVB range (absorbers) other than, of course, the screening agent indicated above. These additional screening agents are advantageously selected, in particular, from among cinnamic derivatives, salicylic derivatives, camphor derivatives, triazine derivatives, benzophenone derivatives, dibenzoylmethane derivatives, β,β-diphenylacrylate derivatives, p-aminobenzoic acid derivatives and the screening polymers and screening silicones described in WO-93/04665. Other examples of organic screening agents are set forth in EP-A-0,487,404.

Too, the compositions according to the invention can contain agents for artificially tanning and/or browning the skin (self-tanning agents), such as, for example, dihydroxyacetone (DHA).

The cosmetic compositions of this invention can also contain nanopigments (average size of the primary particles: generally ranging from 5 nm to 100 nm, preferably from 10 to 50 nm) of coated or uncoated metal oxides, such as, for example, nanopigments of titanium dioxide (amorphous or crystallized in rutile and/or anatase form), of iron oxide, of zinc oxide, of zirconium oxide or of cerium oxide, which are all photoprotective agents that are per se well known and which act by physically blocking out (reflection and/or scattering) the UV radiation. Conventional coating agents are, moreover, alumina and/or aluminum stearate. Such coated or uncoated metal oxide nanopigments are described, in particular, in EP-A-0,518,772 and EP-A-0,518,773.

The cosmetic compositions according to the invention can also be used for protecting the hair and can be formulated as a shampoo, a lotion, a gel, an emulsion, a nonionic vesicle dispersion, a rinse-out composition to be applied before or after shampooing, before or after dyeing or bleaching, before, during or after a permanent-waving or hair-straightening operation, a styling or treating lotion or gel, a blow-drying or hairsetting lotion or gel or a composition for permanent-waving, straightening, dyeing or bleaching the hair.

As above indicated, the present invention also features a cosmetic regime or regimen for the skin or the hair for photoprotecting same against the deleterious effects of UV irradiation rays and which entails topically applying an effective amount of a cosmetic composition consistent herewith onto the skin or the hair.

In order to further illustrate the present invention and the advantages thereof, the following specific examples are given, it being understood that same are intended only as illustrative and in nowise limitative.

EXAMPLES 1 TO 6

Various antisun or sunscreen compositions were formulated as anhydrous solutions containing:

(1) benzotriazole silicone corresponding to compound (a) 5 by weight (2) oil 95% by weight.

The nature of the oil was varied.

For each of the solutions, the UV absorption spectrum ranging from 280 to 400 nm was measured on a UV-visible spectrophotometer: model 552 marketed by Perkin Elmer fitted with a double beam, a UV lamp (deuterium) and a visible lamp (tungsten bromide). The apparatus was equipped with an internal integration sphere also marketed by Perkin Elmer.

Each of the undiluted solutions was spread between two quartz slides, one of which was hollow so as to provide a thickness of 10 μm.

On each of the spectra obtained, the optical density was determined at wavelengths corresponding to the absorption maximum, which are specific to the silicone screening agent containing a benzotriazole function, i.e.: $\lambda_{1max}$=305 and $\lambda_{2max}$=347 nm.

The results obtained are reported in Table A below:

TABLE A

| Example | Oil used | Optical density at 305 nm | Optical density at 347 nm |
|---|---|---|---|
| 1 (invention) | Tridecyl trimellitate (Liponate TDTM marketed by LIPO Chemicals) | 2.19 | 1.82 |
| 2 (prior art) | Phenyltrimethicone (DC 556 marketed by Dow Corning) | 1.77 | 1.67 |
| 3 (prior art) | Glyceryl triheptanoate (Lanol 37T marketed by SEPPIC) | 1.61 | 1.55 |
| 4 (prior art) | $C_{12}$–$C_{15}$ alkyl benzoate (marketed by Stéarineries Dubois) | 1.60 | 1.54 |
| 5 (prior art) | Octyldodecyl neopentanoate (Elefac I 205 marketed by Bernel) | 1.54 | 1.47 |
| 6 (prior art) | Octyldodecanol (Eutanol G marketed by Henkel) | 1.5 | 1.41 |

Compared with the oils of the prior art, these clearly evidence that the presence of tridecyl trimellitate substantially increases the power for absorbing UV radiation of the benzotriazole silicone employed as UV screening agent and dissolved in said oil.

EXAMPLES 7 TO 10

Lipcare sticks:

Three (3) compositions were formulated as lipcare sticks and which contained:

(1) benzotriazole silicone corresponding to compound (a) 5% by weight (2) octacosanyl stearate (wax) marketed under the trademark Kester Wax 82 H by Koster Keunen 10% by weight (3) oil 85% by weight.

The nature of the oil was varied.

For each of the formulations thus prepared, the sun protection factor (SPF) associated therewith was then determined. This was determined using the in vitro technique described by B. L. Diffey et al. in *J. Soc. Cosmet. Chem.*, 40,127–133 (1989); this technique entailed determining the monochromatic protection factors every 5 nm over a wavelength range from 290 to 400 nm and in calculating therefrom the sun protection factor according to a given mathematical equation.

For each of the sticks, the measurements were taken using a UV-visible spectrophotometer—model SPF 290 S marketed by Optometrics—fitted with a UV lamp (xenone) and an integration sphere.

Each of the compositions was applied, in the form of a uniform deposit at a rate of 2 mg/cm$^2$, onto a Transpore adhesive strip marketed by 3M adhered onto a quartz slide.

The compositions of the various formulations studied and the results, in terms of average protection factor, obtained are reported in Table B below:

TABLE B

| Example | Oil used | Average SPF (standard deviation) |
|---|---|---|
| 7 (invention) | Tridecyl trimellitate (Liponate TDTM marketed by Lipo Chemicals) | 6.3 (0.2) |
| 8 (prior art) | Glyceryl triheptanoate (Lanol 37T marketed by SEPPIC) | 5.8 (0.3) |
| 9 (prior art) | $C_{12}$–$C_{15}$ alkyl benzoate (marketed by Stéarineries Dubois) | 4.6 (0.5) |

Compared with the oils of the prior art, these results clearly evidence the appreciable beneficial effect provided by the presence of tridecyl trimellitate in accordance with the invention on the sun protection factors of the final compositions.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological sunscreen composition suited for the UV-photoprotection of human skin and/or hair, comprising (i) a UV-photoprotecting effective amount of at least one solubilized organolipophilic silicon compound bearing a benzotriazole function substituent and (ii) an amount of at least one benzoic triacid triester effective to dissolve said at least one organolipophilic silicon compound.

2. The cosmetic/dermatological sunscreen composition as defined by claim 1, comprising an effective amount of at least one benzoic triacid triester to itself substantially dissolve the total UV-photoprotecting effective amount of said at least one organolipophilic silicon compound.

3. The cosmetic/dermatological sunscreen composition as defined by claim 2, formulated into a topically applicable, cosmetically/dermatologically acceptable vehicle, diluent or carrier therefor.

4. The cosmetic/dermatological sunscreen composition as defined by claim 1, said at least one organolipophilic benzotriazole-substituted silicon compound comprising at least one structural unit having the formula (1):

$$O_{(3-a)/2}Si(R_1)_z\text{-}G \quad (1)$$

in which $R_1$ is an optionally halogenated $C_1$–$C_{10}$ alkyl radical, or a phenyl or trimethylsilyloxy radical; a is an integer ranging from 0 to 3, inclusive; and the symbol G is a monovalent radical directly bonded to a silicon atom and having the structural formula (2) below:

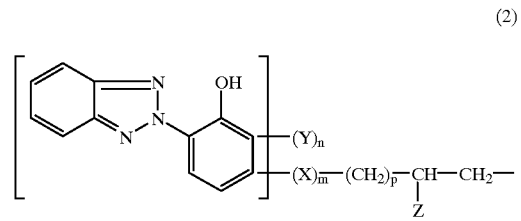

(2)

in which the radicals Y, which may be identical or different, are each a $C_1$–$C_8$ alkyl radical, a halogen atom, or a $C_1$–$C_4$ alkoxy radical, with the proviso that, in the latter instance, two adjacent groups Y on the same aromatic ring member can together form an alkylidenedioxy group wherein the alkylidene group contains 1 or 2 carbon atoms; X is O or NH; Z is hydrogen or a $C_1$–$C_4$ alkyl radical; n is an integer ranging from 0 to 3, inclusive; m is 0 or 1; and p is an integer ranging from 1 to 10, inclusive.

5. The cosmetic/dermatological sunscreen composition as defined by claim 4, said at least one organolipophilic benzotriazole-substituted silicon compound having the structural formula (3) or (4):

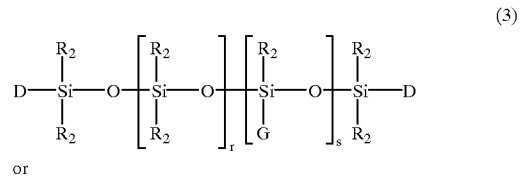

(3)

or

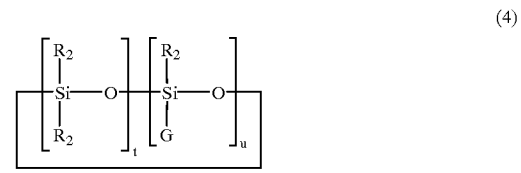

(4)

in which the radicals $R_2$, which may be identical or different, are each a $C_1$–$C_{10}$ alkyl, phenyl, 3,3,3-trifluoropropyl or trimethylsilyloxy radical, at least 80% by number of the radicals $R_2$ being methyl radicals; the radicals D, which may be identical or different, are each a radical $R_2$ or the radical G; r is an integer ranging from 0 to 50, inclusive, and s is an integer ranging from 0 to 20 inclusive, and if s=0, at least one of the two radicals D is a radical G; u is an integer ranging from 1 to 6, inclusive, and t is an integer ranging from 0 to 10, inclusive, with the proviso that t+u is greater than or equal to 3.

6. The cosmetic/dermatological sunscreen composition as defined by claim 5, said at least one organolipophilic benzotriazole-substituted silicon compound having the structural formula (5):

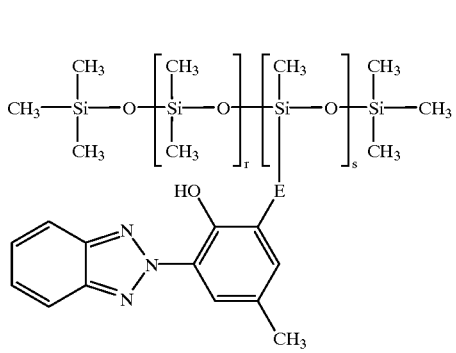

in which $0 \leq r \leq 10$; $1 \leq s \leq 10$; and E is the divalent radical:

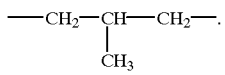

7. The cosmetic/dermatological sunscreen composition as defined by claim 5, said at least one organolipophilic benzotriazole-substituted silicon compound having the structural formula:

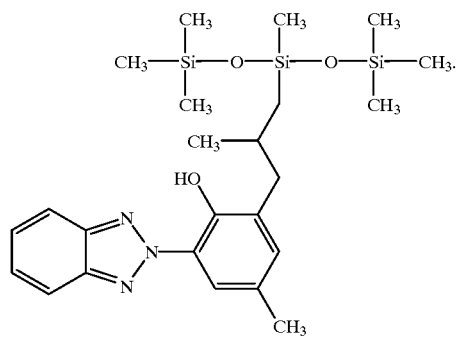

8. The cosmetic/dermatological sunscreen composition as defined by claim 1, comprising from 0.1% to 20% by weight of said at least one organolipophilic benzotriazole-substituted silicon compound.

9. The cosmetic/dermatological sunscreen composition as defined by claim 8, comprising from 0.2% to 15% by weight of said at least one organolipophilic benzotriazole-substituted silicon compound.

10. The cosmetic/dermatological sunsreen composition as defined by claim 1, said at least one benzoic triacid triester having the structural formula (I):

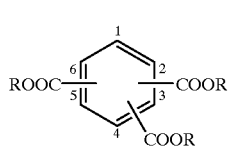

in which R is a linear or branched, saturated or unsaturated alkyl radical having from 3 to 30 carbon atoms.

11. The cosmetic/dermatological sunscreen composition as defined by claim 10, wherein formula (I), R has from 8 to 18 carbon atoms.

12. The cosmetic/dermatological sunscreen composition as defined by claim 10, said at least one benzoic triacid triester comprising a trimellitic acid triester having the structural formula (II):

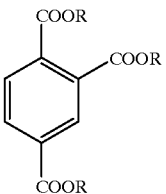

in which R is a linear or branched, saturated or unsaturated alkyl radical having from 3 to 30 carbon atoms.

13. The cosmetic/dermatological sunscreen composition as defined by claim 12, said at least one trimellitic acid triester comprising 2-ethylhexyl trimellitate, decyl trimellitate, triisodecyl trimellitate, 2-butylhexyl trimellitate, tridecyl trimellitate, or mixture thereof.

14. The cosmetic/dermatological sunscreen composition as defined by claim 10, comprising from 0.1% to 99% by weight of said at least one benzoic triacid triester.

15. The cosmetic/dermatological sunscreen composition as defined by claim 14, comprising from 0.5% to 50% by weight of said at least one benzoic triacid triester.

16. The cosmetic/dermatological sunscreen composition as defined by claim 1, having a sun protection factor of at least 2.

17. The cosmetic/dermatological sunscreen composition as defined by claim 1, comprising an oil-in-water emulsion.

18. The cosmetic/dermatological sunscreen composition as defined by claim 1, comprising a water-in-oil emulsion.

19. The cosmetic/dermatological sunscreen composition as defined by claim 1, further comprising at least one additional hydrophilic or lipophilic UVA- and/or UVB-sunscreen.

20. The cosmetic/dermatological sunscreen composition as defined by claim 19, further comprising at least one cinnamic sunscreen, salicylic sunscreen, camphor sunscreen, benzophenone sunscreen, dibenzoylmethane sunscreen, triazine sunscreen, β,β'-diphenylacrylate sunscreen, p-aminobenzoic acid sunscreen, sunscreen polymer and/or sunscreen silicone other than one benzotriazole-substituted.

21. The cosmetic/dermatological sunscreen composition as defined by claim 1, further comprising at least one active agent for the artificial tanning and/or browning of human skin.

22. The cosmetic/dermatological sunscreen composition as defined by claim 1, further comprising at least one cosmetically/dermatologically acceptable adjuvant or additive.

23. The cosmetic/dermatological sunscreen composition as defined by claim 22, said at least one adjuvant or additive comprising a fat, organic solvent, ionic or nonionic thickening agent, softener, antioxidant, anti-free-radical antioxidant, opacifying agent, stabilizing agent, emollient, silicone, fluoro compound, hydroxy acid, antifoaming agent, vitamin, fragrance, preservative, surfactant, filler, sequestering agent, pearlescent agent, hydrating agent, polymer, propellant, basifying or acidifying agent, dye, colorant, or mixture thereof.

24. The cosmetic/dermatological sunscreen composition as defined by claim 1, further comprising a photoprotecting effective amount of particulates of at least one inorganic pigment or nanopigment.

25. The cosmetic/dermatological sunscreen composition as defined by claim 24, said at least one pigment or nanopigment comprising titanium dioxide, zinc oxide, iron oxide, zirconium oxide, cerium oxide, or mixture thereof.

26. The cosmetic/dermatological sunscreen composition as defined by claim 1, comprising a nonionic vesicle dispersion, lotion, cream, milk, gel, salve, cream gel, ointment, suspension, dispersion, powder, solid stick, foam or spray.

27. The cosmetic/dermatological sunscreen composition as defined by claim 1, comprising a makeup.

28. The cosmetic/dermatological sunscreen composition as defined by claim 1, comprising a liquid, solid or paste.

29. The cosmetic/dermatological sunscreen composition as defined by claim 1, comprising a shampoo, rinse, styling lotion or gel, blow-drying or hairsetting lotion or gel, or permanent-waving, straightening, dyeing or bleaching composition for the hair.

30. The cosmetic/dermatological sunscreen composition as defined by claim 1, comprising a foundation, lipstick, mascara, eyeshadow, eyeliner, or nail varnish.

31. A regime/regimen for photoprotecting human skin and/or hair against the deleterious effects of ultraviolet radiation, comprising topically applying thereto an effective amount of the cosmetic/dermatological sunscreen composition as defined by claim 1.

32. A regime/regimen for photoprotecting human skin and/or hair against the deleterious effects of solar radiation, comprising topically applying thereto an effective amount of the cosmetic/dermatological sunscreen composition as defined by claim 1.

* * * * *